United States Patent
Raguse et al.

(10) Patent No.: US 6,291,155 B1
(45) Date of Patent: Sep. 18, 2001

(54) SELF ASSEMBLY OF SENSOR MEMBRANES

(75) Inventors: Burkhard Raguse, St. Ives; Ronald John Pace, Homebush; Lionel George King, Morefield; Vijoleta Lucija Braach-Maksvytis, Dulwich Hill; Bruce Cornell, Neutral Bay, all of (AU)

(73) Assignee: Australian Membrane and Biotechnology Research Institute, Chattsworth (AU)

( * ) Notice: Subject to any disclaimer, the term of this patent is extended or adjusted under 35 U.S.C. 154(b) by 0 days.

(21) Appl. No.: 09/262,098

(22) Filed: Mar. 4, 1999

Related U.S. Application Data

(62) Division of application No. 08/685,329, filed as application No. PCT/AU96/00369 on Jun. 20, 1996, now Pat. No. 5,879,878.

(30) Foreign Application Priority Data

Jun. 20, 1995 (AU) .................................................... PN3669

(51) Int. Cl.[7] ................................................ G01N 33/553
(52) U.S. Cl. ............................. 435/4; 204/400; 204/403; 422/82.01; 422/82.03; 427/2.11; 427/2.13; 435/7.5; 435/287.1; 435/287.2; 436/525; 436/806
(58) Field of Search .................................. 204/400, 403; 422/82.01, 82.03; 435/7.5, 4, 287.1, 287.2; 436/525, 806; 427/2.11, 2.13

(56) References Cited

U.S. PATENT DOCUMENTS

| | | | |
|---|---|---|---|
| 4,824,529 | * | 4/1989 | Thompson et al. ................. 204/403 |
| 5,204,239 | * | 4/1993 | Gitler et al. ......................... 435/7.1 |
| 5,234,566 | * | 8/1993 | Osman et al. ...................... 204/403 |
| 5,286,365 | * | 2/1994 | Shu ..................................... 204/418 |
| 5,328,847 | * | 7/1994 | Case et al. .......................... 435/817 |
| 5,401,378 | * | 3/1995 | King et al. .......................... 204/418 |
| 5,436,170 | * | 7/1995 | Cornell et al. ..................... 436/527 |
| 5,443,955 | * | 8/1995 | Cornell et al. .................... 435/7.21 |
| 5,591,647 | * | 1/1997 | King ................................... 436/518 |
| 5,637,201 | * | 6/1997 | Raguse et al. ...................... 204/418 |

FOREIGN PATENT DOCUMENTS

| | | | |
|---|---|---|---|
| 5144493 | * | 4/1994 | (AU) . |
| 93/21528 | * | 10/1993 | (WO) . |

* cited by examiner

Primary Examiner—Christopher L. Chin
(74) Attorney, Agent, or Firm—Gottlieb, Rackman & Reisman, P.C.

(57) ABSTRACT

Electrode membrane combinations for use in biosensors to detect analytes in a sample and methods for making and storing same are disclosed. In one aspect, a method is provided for producing a first layer electrode membrane comprising:

(1) Forming a solution containing Linker Lipid A, the disulfide of mercaptoacetic acid (MAAD) or similar molecule, linker Gramicidin B, membrane spanning lipid C (MSL-C) and membrane spanning lipid D (MSL-D) or other suitable linker molecules and other ion channel combinations;

(2) Contacting an electrode containing a clean gold surface with the solution, the disulfide containing components in the solution thus adsorbing onto the gold surface of the electrode;

(3) Rinsing the electrode with a suitable organic solvent; and (4) Removing the excess organic solvent used for rinsing.

40 Claims, 15 Drawing Sheets

LINKER LIPID A

LINKER GRAMICIDIN B

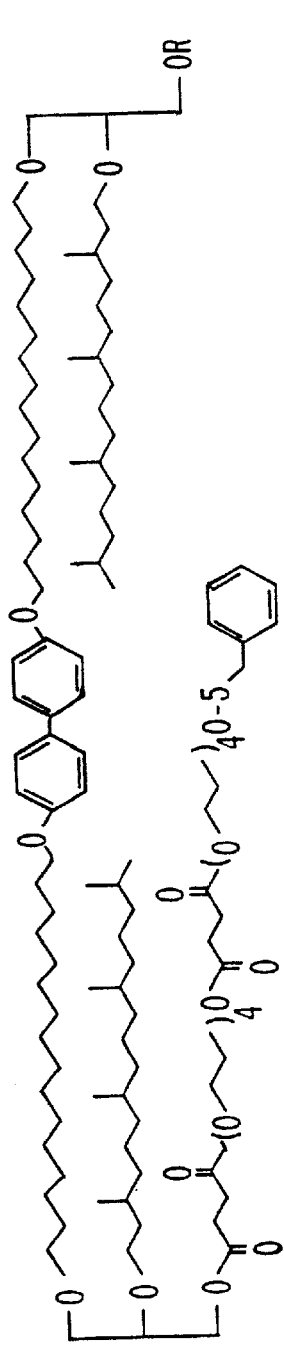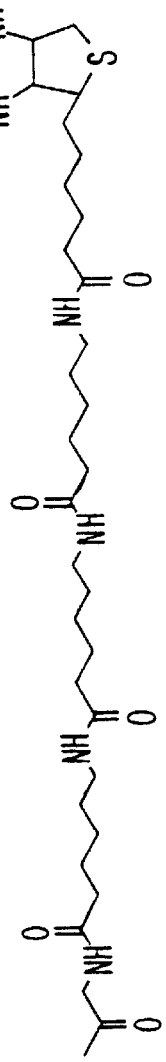
FIG. 3

BIOTINYLATED GRAMICIDIN E

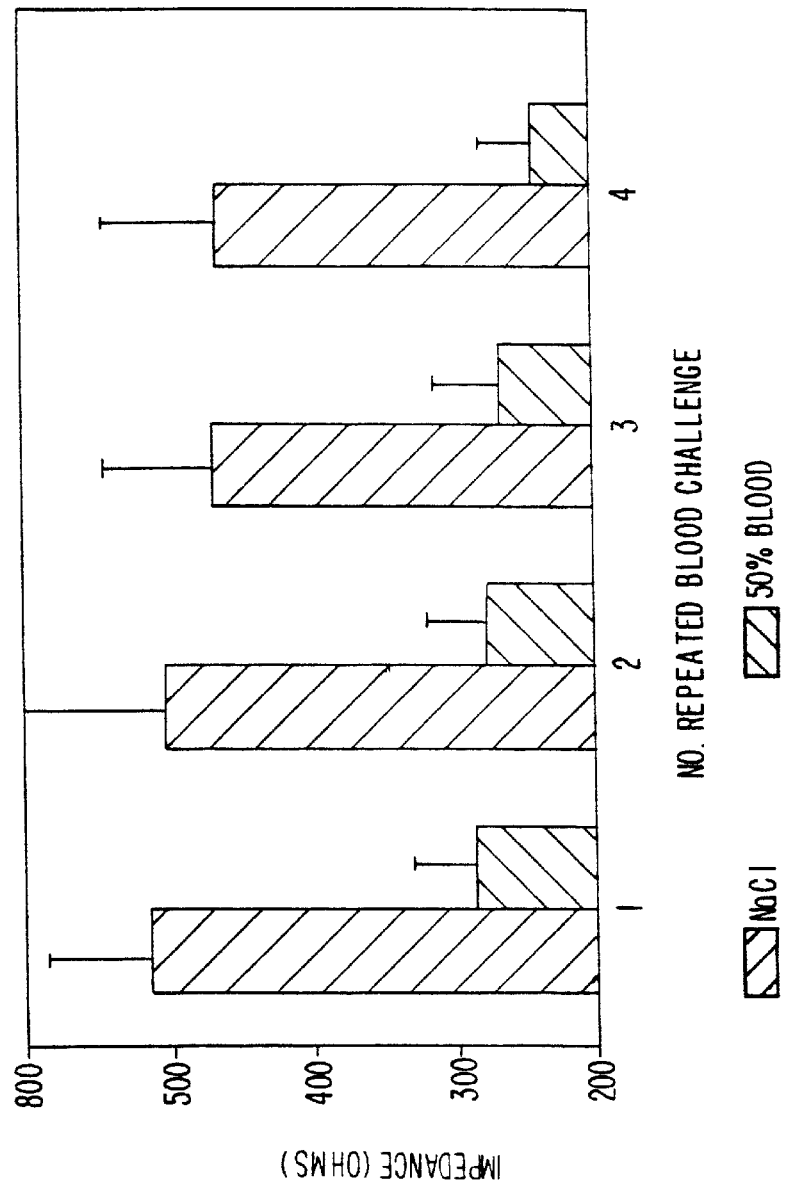

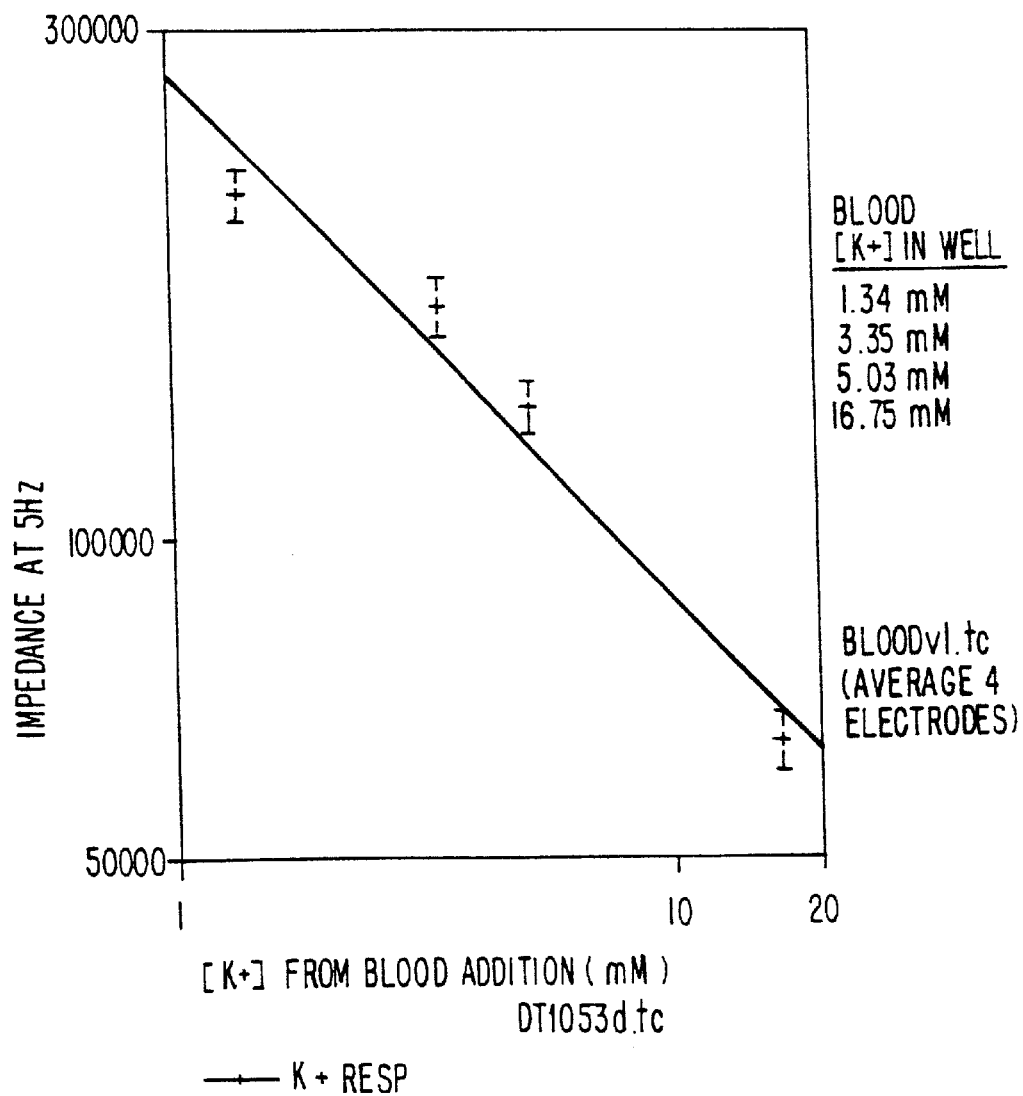

SA TITRATION WITH VARIOUS GaX..B

METHOD: 5/4 MEMBRANES
1st LAYERS: 10 mM GMPE
　　　　　　 1 mM DLP
　　　　　　 10 uM MSLXXB
　　　　　　 0.8 mM MAAD
　　　　　　 0.1 uM GaYYSS
2nd LAYERS: 28 mM GMPE
　　　　　　 0.28 uM GaX..B CHOSEN FROM THE FOLLOWING:
　　　　　　 GaXB
　　　　　　 GaXXB
　　　　　　 GaXXXB
　　　　　　 Ga(XXXB)$_2$ (1) BEFORE THE ADDITION OF GRAMICIDIN/SDS
(2) AFTER THE ADDITION OF GRAMICIDIN/SDS; STREPTAVIDIN AND BIOTINYLATED FAB'
(3) AFTER THE ADDITION OF FERRITIN (1) BEFORE ADDITION OF GRAMICIDIN/STREPTAVIDIN
(2) AFTER ADDITION OF GRAMICIDIN/STREPTAVIDIN AND BIOTINYLATED FAB'S
(3) AFTER ADDITION OF TSH

SELF ASSEMBLY OF SENSOR MEMBRANES

This is a division of application Ser. No. 08/865,329, filed Jul. 23, 1996, now U.S. Pat. No. 5,879,878, which is the U.S. nations stage of PCT/AU96/0369, filed Jun 20, 1996.

The present invention relates to electrode membrane combinations for use in biosensors to detect analytes in a sample and to methods for the production of such electrode membrane combinations. The present invention also relates to methods for storing such electrode membrane combinations.

Biosensors based on ion channels or ionophores contained within lipid membranes that are deposited onto metal electrodes and where the ion channels are switched in the presence of analyte molecules have been described in International patent specification Nos WO 92/17788, WO 93/21528, WO 94/07593 and U.S. Pat. No. 5,204,239 (the disclosures of which are incorporated herein by reference). As is disclosed in these applications, ionophores such as gramicidin ion channels may be co-dispersed with amphiphilic molecules, thereby forming lipid membranes with altered properties in relation to the permeability of ions. There is also disclosure of various methods of gating these ion channels (for example, the lateral segregation mechanism disclosed in International Patent Application WO90/08783) such that in response to the binding of an analyte to a binding partner attached to the membrane, the conductivity of the membrane is altered. The applications also disclose methods of producing membranes with improved sensitivity using a surface amplifier effect, and improved stability and ion flux using chemisorbed arrays of amphiphilic molecules attached to an electrode surface. The applications further disclose means of producing lipid membranes incorporating ionophores on said chemisorbed amphiphilic molecules.

The present inventors have now determined improved means of producing electrode membrane combinations that result in sensor membranes with improved properties in terms of reproducibility; gating response towards an analyte, lateral segregation response, surface amplifier effect, stability in serum, plasma and blood, simplified production and the ability to store the membranes in a dry format (i.e. in the absence of any aqueous bath solution).

In the first aspect, the present invention consists in a method of producing a first layer electrode membrane comprising:

(1) Forming a solution containing Linker Lipid A (FIG. 1), the disulfide of mercaptoacetic acid (MAAD) or similar molecule, such as EDS linker Gramicidin B (FIG. 2), membrane spanning lipid C (MSL-C) (FIG. 3) and membrane spanning lipid D (MSL-D) (FIG. 3) or other linker molecules and ion channel or ionophore combinations as previously described;
(2) Contacting an electrode containing a clean gold surface with the solution, the disulfide containing components in the solution thus adsorbing onto the gold surface of the electrode;
(3) Rinsing the electrode with a suitable organic solvent; and
(4) Removing the excess organic solvent used for rinsing.

The nature of the membrane components are as follows:

Linker Lipid A comprising a benzyl disulfide attachment region, a hydrophilic region composed, in sequence, of tetraethylene glycol, succinic acid, tetraethylene glycol and succinic acid subgroups and an aliphatic chain;

The disulfide of mercaptoacetic acid (MAAD) or similar molecule, such as the disulfide of 2-mercaptoethanol (EDS).

Linker Gramicidin B is a linker molecule which comprises a benzyl disulfide attachment region, a hydrophilic region composed, in sequence, of tetraethylene glycol, succinic acid, tetraethylene glycol, succinic acid, and a hydrophobic region of gramicidin;

Membrane spanning lipid (MSL) D which comprises a benzyl disulfide attachment region, a hydrophilic region composed, in sequence, of tetraethylene glycol, succinic acid, tetraethylene glycol, succinic acid and a hydrophobic region of 1,1'dotriacontamethylenebis (2–3 RS,7R, 11-phytanyl) with an intermediate biphenyl region and a head group of phosphatidylcholine, hydroxyl, succinic acid, or PEG-400 COOH; and Membrane spanning lipid C which comprises the same attachment and hydrophilic region as membrane spanning lipid D but differs in the head group which is a group consisting of (one to eight) 1,.6-amino caproic acid and biotin.

In a preferred embodiment of the present invention the ratio of Linker Lipid A to the disulfide of mercaptoacetic acid (MAAD) or 2-mercaptoethoethanol (EDS) is 5:1 to 1:2. more preferably is 2:1.

It is further preferred that in order to improve the stability of the membrane. Theme amount of MSL-D in the first layer is as high as can be allowed and still maintain reasonable gramicidin conduction. The ratio of (Linker Lipid A+MAAD or EDS) to MSL-D is therefore preferably between 10:1 to 100:1.

In a further preferred embodiment, the amount of MSL-C is such that in the final sensor membrane an effective surface amplification on addition of analyte occurs, while still making it possible to suppress the lateral segregation induced gating on addition of the streptavidin, avidin or other similar biotin-binding protein. It should be noted that if the amount of MSL-C in the final sensor membrane is too large,. then the excess protein that is bound to MSL-C on addition of the streptavidin, avidin or similar biotin-binding protein will restrict the mobility of the gramicidin/receptor couple thereby reducing the gating response. In cases where the analyte molecule has multiple identical epitopes, MSL-C may capture the analyte molecules in preference to gramicidin/receptor couple, reducing the biosensor response.

It is therefore preferred that the ratio of (Linker Lipid A+MAAD or EDS) to membrane spanning lipid C is between 20,000:1 and 100:1.

It is further preferred that the ratio of (Linker Lipid A+MAAD or EDS) to MSL-C is 20,000:1.

As is known in the art, gramicidin exists in a monomer/dimer equilibrium in a bilayer membrane. In order for the gramicidin lateral segregation switch to function effectively, the ratio of monomer to dimer must be controlled. It is preferred that a proportion of the gramicidin ion channels exist as freely diffusing monomers in the outer membrane layer. The ratio of monomers to dimers can be controlled, amongst other methods, by changing the concentration of gramicidin in the first and second half of the membrane.

It is therefore preferred that the ratio of (Linker Lipid A+MAAD or EDS) to linker Gramicidin B is 10.000:1.

It is further preferred that the ratio of (Linker Lipid A+MAAD or EDS) to linker Gramicidin B is between 20.000:1 and 100,000:1 in those cases where it is necessary to minimise the amount of background leakage due to the adsorbed linker Gramicidin B.

It is preferred that the gold electrode consists of a freshly evaporated or sputtered gold electrode. It is further preferred that the gold electrode surface be freshly cleaned using a plasma etching process or an ion beam milling process.

It is preferred that the solvent for the adsorbing solution (step (1) and for the rinsing step (4) is ethanol.

In a second aspect, the present invention consists in a method of producing a monolayer electrode membrane comprising:
(1) Forming a solution containing the disulfide of mercaptoacetic acid (MAAD) or similar molecule (e.g. 2-mercaptoethanol (EDS)), membrane spanning lipid C(MSL-C) and/or membrane spanning lipid D (MSL-D) and, optionally. Linker Lipid A. linker Gramicidin B or other linker molecules or ion channel or ionophore combinations;
(2) Contacting an electrode containing a clean gold surface with the solution, the disulfide containing components in a solution thus adsorbing onto the gold surface of the electrode;
(3) Rinsing the electrode with a suitable organic solvent; and
(4) Removing the excess organic solvent used for rinsing, wherein the solution in step (1) contains more than a molar % of 50% of a membrane spanning lipid.

More preferably, the solution in step (1) contains more than a molar % or 70% of a membrane spanning lipid, 29% MAAD or EDS and 1% other membrane spanning lipids.

The preferred features and embodiments discussed above in regard to the method of the first aspect of the invention, may be equally applicable to the method of the second aspect of the invention.

The membranes produced by the method of the second aspect of the invention, do not form bilayers and have been found to be particularly resistant towards non-specific effects on addition of serum, plasma or whole blood to the sensor. Further advantages have been noted in that these membranes may be reused over a period of months in serum, plasma or whole blood without showing signs of degradation of performance. Monolayer lipid membranes are more practical for manufacturing purposes, have fewer manufacturing steps and greater stability, leading to a later expiry on the manufactured sensor containing such membranes. In this it is also preferable for the spacer molecule, MAAD or EDS, to be covalently linked to the membrane spanning lipids C or D, and covalently linked to PEPC, GDPE or triphytanyl PC, which increases stability of the final membrane.

A further preferred embodiment of the method according to the second aspect of the invention, consists in the use of valinoycin, covalently linked to the membrane spanning lipids C or D, via a linker of appropriate length such that the valinomycin is able to diffuse from one side of the membrane to another. This then results in a reusable biosensor, which does not need replenishment of the ionophore and could be used for an implantable device.

The present inventors have determined that the production of the biosensor is simplified and improved through the use of streptavidin, avidin or one of the related biotin binding-proteins as a means of coupling a biotinylated receptor onto a biotinylated gramicidin ion channel or MSL.

In a third aspect, the present invention consists in a method of producing a second layer electrode membrane combination utilising biotinylated gramicidin E, in which the biotin is attached to the gramicidin via an amide to a lysine residue (preferred for chemical stability) or via an ester link to ethanolamine using a linker arm that is made up of between 1 to 8 aminocaproyl groups. The linker length, type, valency and number of linkers can affect the stability of the completed sensor and the optimum linker varies depending on the analyte being measured. The method comprises:
(1) Adding a solution of lipid and biotinylated gramicidin E (FIG. 4), dispersed in a suitable solvent onto the electrode surface containing a first layer produced as described in the first aspect of the present invention;
(2) Rinsing the electrode surface with an aqueous solution;
(3) Adding a solution of streptavidin, avidin, neutravidin, avidin or streptavidin derivative;
(4) Rinsing the electrode with an aqueous solution in order to remove excess streptavidin, avidin, neutravidin other avidin or streptavidin derivative;
(5) Adding a solution of a biotinylated binding partner molecule; and
(6) Rinsing the coated electrode with an aqueous solution. In a preferred embodiment of the present invention the lipid used in step (1) of the method of the third aspect is a mixture of diphytanyl phosphatidyl choline and glyceryl diphytanyl ether. The inventors have found that the combination of these lipids improves the stability of the bilayer membrane towards serum, plasma and whole blood, while still maintaining a good ionic seal, fluidity, reducing temperature effects on conduction and maintaining a true bilayer membrane structure.

It is further preferred that the diphytanyl phosphatidyl choline (DPEPC) and glyceryl diphytanyl ether (GDPE) is in a 7:3 ratio.

It is further preferred that the lipid is a triphytanyl phosphoryl choline as shown in FIG. (6).

It is also preferred that membranes contain 0 to 50%, more preferably 0 to 20% cholesterol in the second layer to enhance stability and analyte response in a serum, plasma or whole blood sample.

It is preferred that the ratio of lipid to biotinylated gramicidin E is between 10,000:1 and 1,000,000:1.

It is further preferred that the ratio of lipid to biotinylated gramicidin E is 100,000:1.

It is preferred that the biotin is attached to the gramicidin via the ethanolamine end using a linker arm that is between 10–80 angstroms long. It is preferred that the linker arm is hydrophilic.

It is preferred that the biotin is attached to the gramicidin via the ethanolamine end using a linker arm that is made up of between 1 to 8 aminocaproyl groups.

It is further preferred that two biotins are attached to the gramicidin via the ethanolamine end such that the biotins are able to bind simultaneously into the adjacent binding sites of one streptavidin, avidin or similar biotin-binding protein molecule, or into two separate streptavidin avidin or similar biotin-binding protein molecules. Alternatively, more than two biotin molecules can be attached to the gramicidin to produce multiple attachment sites for the binding partner molecules.

It is preferred that the two biotins are attached to the gramicidin via the ethanolamine end such that each biotin is attached to two to four linearly joined aminocaproyl groups that are attached to a lysine group as shown in FIG. (5). When more than two biotin molecules are attached to the gramicidin, a longer linker up to twenty aminocaproyl groups may be necessary these may be organised linearly or as a branched structure.

It is further preferred that in order to optimise the analyte response, it is necessary to minimise the signal caused by the presence of the linker. Thus, the amount of streptavidin, avidin or other similar biotin-binding protein that is added in step (3) is sufficient to cause a prozone effect, allowing most of the available biotinylated species in the membrane to have one streptavidin or related molecule bound to prevent crosslinking between gramicidin channels and MSL until a sample containing analyte is added to the sensor.

It is further preferred that prior to the addition of the streptavidin, avidin, or similar biotin-binding protein the lipid membrane electrode assembly is cooled. This reduces the fluidity of the membrane, decreasing the mobility of membrane components thus allowing the streptavidin, avidin or other similar biotin-binding protein to more readily bind to the biotinylated Gramicidin E and the membrane spanning lipid C without crosslinking between gramicidin channels and MSL until a sample containing analyte is added to the sensor.

It is preferred that the lipid membrane electrode is cooled to between 0° and 50° C. more preferably 0° and 5° C. It is further preferred that the subsequent rinsing and addition of the biotinylated binding partner molecule are also carried out at 0° to 50° C. more preferably 0° to 5° C.

It is preferred that the binding partner molecule is a biotinylated antibody or biotinylated antibody fragment.

It is further preferred that the binding partner molecule is a Fab' fragment that is biotinylated via the free Fab' thiol group.

Is further preferred that the linker between the Fab' and biotins is between 10–80 angstroms in length. Is further preferred that the linker between the Fab' and biotins consists of one to eight aminocaproyl groups.

It is further preferred that the group containing two biotins is attached to the antibody or antibody fragment such that the two biotins are able to complex simultaneously one streptavidin, avidin or other similar biotin-binding protein or two adjacent streptavidin, avidin or other similar biotin-binding protein molecules Alternatively, more than two biotins may be attached to the antibody or antibody fragment.

Furthermore, the present inventors have determined that by producing a covalently or passively coupled conjugate between the binding partner molecule and the streptavidin, avidin or other similar biotin binding protein the production of the biosensor membrane is further simplified.

Accordingly, steps 3 to 5 of the method of the third aspect can be substituted with:
(3) Adding a solution containing a conjugate between streptavidin, avidin, neutravidin or other avidin or streptavidin derivative and a molecule which is a member of a binding pair.

It is preferred that the binding partner molecule is an antibody or an antibody fragment such as an Fab or Fab' or Fv fragment. Other binding pairs, which could be used in this invention would include: naturally occurring binding proteins and cellular receptors/analytes, enzymes or enzyme analogues/substrates, lectins/carbohydrates, complementary nucleic acid sequences and Anti-FC, Protein A or Protein G/antibody.

In order to manufacture sensor membranes efficiently and reproducibly, it is advantageous to incorporate the ionophore separate to the assembled membrane. It is also advantageous to bind one binding partner to the ionophore, before incorporation into the membrane. This both controls and enhances the reproducibility of membrane conduction and allows the reproducible attachment of the second binding partner needed in a two site immuno- or similar assay system, ensuring that only the first binding partner is attached to ionophore and only the second binding partner is attached to a second ionophore or MSL.

The present inventors have found that it is possible to co-disperse the hydrophobic ionophore in aqueous solution by several means, including:
1. The presence of a detergent, preferably at levels below the critical micelle concentration of the detergent, such that ionophore and the detergent form aggregates which allow the ionophore to remain in solution;
2. Conjugation of the gramicidin or other ionophore to a large molecular weight water soluble species; and
3. Attachment of the ionophore to a bead.

Furthermore it was found that it was possible to incorporate the functional ionophore into the biosensor lipid membranes by adding an aqueous solution of the ionophore/detergent aggregate to the solution bathing the preformed lipid biosensor membrane. This method of addition of the ionophore allows for a more controlled and reproducible method of incorporation of the ionophore into the lipid membrane.

Accordingly, in a fourth aspect, the present invention consists in a method of producing a second layer electrode membrane combination comprising:
(1) Adding a solution of lipid dispersed in a suitable solvent onto the electrode surface containing a first layer produced as described in the method of the first aspect of the present invention;
(2) Rinsing the electrode surface with an aqueous solution;
(3) Adding an aqueous solution containing ionophore co-dispersed with detergent or solubilised by coupling to a high molecular weight soluble species;
(4) Rinsing the electrode with an aqueous solution; and
(5) Adding the receptor using either streptavidin, avidin, or other similar biotin-binding protein followed by addition of a biotinylated antibody or antibody fragment or adding a streptavidin, avidin or similar biotin-binding protein conjugated to an antibody or antibody fragment as detailed in the third aspect of the present invention.

In a preferred embodiment of the present invention the lipid used in step (1) is a mixture of diphytanyl phosphatidyl choline and glyceryl diphytanyl ether. It has been found that the combination of these lipids improves the stability of the bilayer membrane towards serum, plasma and whole blood, while still maintaining a good ionic seal, fluidity, reducing temperature effects on conduction and maintaining a true bilayer membrane structure.

It is further preferred that the diphytanyl phosphatidyl choline and glyceryl diphytanyl ether is in a 7:3 ratio.

It is further preferred that the lipid is a triphytanyl phosphoryl choline as shown in FIG. (6).

It is also preferred that membranes contain 0 to 50%, more preferably up to 20% cholesterol in the second layer to enhance stability and analyte response in a serum, plasma or whole blood sample.

It is preferred that the aqueous solution used in step (3) of the fourth aspect of the present invention, contains gramicidin or a gramicidin derivative that is added to an aqueous solution of a detergent such that the detergent is present in excess relative to the gramicidin but that the total concentration of detergent is below the critical micelle concentration (CMC). The total detergent concentration is preferably kept below the CMC in order to minmise or negate any possible disruption of the membrane by the detergent.

The gramicidin/detergent solution is then preferably sonicated using an ultrasonic bath or horn for 5 to 20 minutes.

Preferred detergents are sodium dodecylsulfate, octyglucoside, tween, or other ionic or non-ionic detergents.

It is further preferred that the alkyl chain contains at least 7 or more methylene groups.

It is preferred that the detergent is sodium dodecylsulfate.

It is further preferred that the concentration of the sodium dodecylsulfate is less than 0.00001M and that the concentration of gramicidin is ten times less than the sodium dodecylsulfate concentration.

It has been found that, if it is necessary to store the electrodes which already have the first layer of the membrane adsorbed onto the electrode surface, then it is advantageous to store said electrodes covered in a solvent. This method of storing the electrode with the first layer membrane in a solution has been found to produce subsequent sensor membranes with improved homogeneity and ionophore gating ability, compared with storing the electrode in air.

Accordingly,. in a fifth aspect the present invention consists in a first layer membrane electrode combination comprising an electrode and a first layer membrane comprising a closely packed array of amphiphilic molecules and a plurality of ionophores, the first layer membrane being connected to the electrode by means of a linker group as described previously, said first layer membrane being stored in the presence of a solvent.

Electrodes may be stored in a gaseous or liquid environment and, in a preferred embodiment, the solvent in which the electrodes are stored is an organic solvent or an aqueous solvent.

If the solvent is an organic solvent, it is further preferred that the solvent is an alcohol such as ethanol, glycerol, ethylene nicglycol, an alcohol or diol containing between 3 to 12 carbon atoms.

It is further preferred that the solvent is a hydrocarbon with between 8 to 20 carbon atoms. It is further preferred that the solvent is an aqueous solution containing a detergent.

It is further preferred that the solvent is a compound that is able to coat the electrodes such that oxidation of the electrode surface is minimised. It is preferred that such a solvent can be applied as a thin film.

Additionally it has been found that it is possible to store the complete sensor membrane electrode combination in a non-aqueous format. This is highly advantageous in terms of ease of manufacturing, shipping and storing of the biosensor product.

Accordingly, in a sixth aspect, the present invention consists in a lipid membrane based biosensor comprising a lipid membrane incorporating ionophores, the conductivity of the membrane being dependent on the presence or absence of an analyte, wherein the aqueous bathing solution in which the biosensor normally resides, is removed in a manner such that, on drying of said lipid membrane biosensor, the lipid membrane and the receptor molecules retain their function, structure and activity, when rehydrated.

It is preferred that in the drying process that the biosensor membrane does not have contact with the air-water interface, hence methods of drying such as lyophilisation, evaporation, or evaporation over controlled humidity, are recommended. It is also preferred that the concentration of the water-replacing agent is sufficient to protect all components within the membrane, i.e. lipid, ionophore and protein, during the drying process, during the storage time, and yet is easily removed upon the first addition of analyte or sample in the appropriate matrix, such that full activity of the biosensor membrane is restored immediately.

The water replacing substance may be either a protein, a low molecular weight diol or triol, a polyethylene glycol, a low molecular weight sugar, a polymeric peptide, polyelectrolyte or combinations of these substances, all of which are well known in the art. The main attributes of the water substitute are that it is highly polar, has a low vapour pressure, allows the membrane to retain its structure, is protein compatible and does not impede biosensor function when rehydrated. These substances may also be covalently bound to a specific membrane component, preferably a membrane spanning lipid.

It is preferred that the water replacing substance is bovine serum albumin, serum, fish gelatin, non-fat dry milk powder, casein, glycerol, ethylene glycol, diethylene glycol, polyethylene glycol, trehalose, xylose, glucose, sucrose, dextrose, ficoll and it is further preferred that the water replacing molecule is glvcerol, sucrose, dextran or trehalose.

Such classes of molecules may also have the additional advantage in the biosensor to act as a spreading layer for serum/blood/analyte fluid addition; as a filter against specific cells, bacteria, virus particles, or classes of molecules; or as a reservoir containing specific displacement reagents required to compete off small analytes from proteins to which they are bound in serum or blood.

A further advantage of the water substituting agent is that it allows for the controlled rehydration of the lipid membrane without the lipid bilayer being in contact with the air/water interface as the analyte solution or sample is added.

An example of the latter is given in FIG. 13, where water-replacing molecules are either added or covalently bound to regions of the membrane and contain, for example, ANS (8-anilino-1-naphthalene-sulfonic acid) which competes with thyroxine for binding sites in albumin and thyroxine-binding globulin (TBG), releasing thyroxine for subsequent detection by the biosensor membrane."

The invention is hereinafter further described with reference to the following non-limiting examples and accompanying figures.

BRIEF DESCRIPTION OF THE FIGURES

FIG. 3 shows membrane spanning lipids C and D. Membrane spanning lipid C terminates in a group consisting of between one to eight 1.6-amino caproic groups and biotin. Membrane spanning lipid D comprises the head group which is a group consisting of phosphatidylcholine (PC), OH, succinic acid or polyethylene glycol (PEG) 400.

FIGS. 7A–7G shows the impedance change of the biosensor owing to K+ in human blood.

FIG. 8 shows repeated whole blood K+ detection in monolayer biosensor membrane.

FIG. 9 shows that the biosensor response in whole blood was a function of the K+ concentration.

Figure 1:
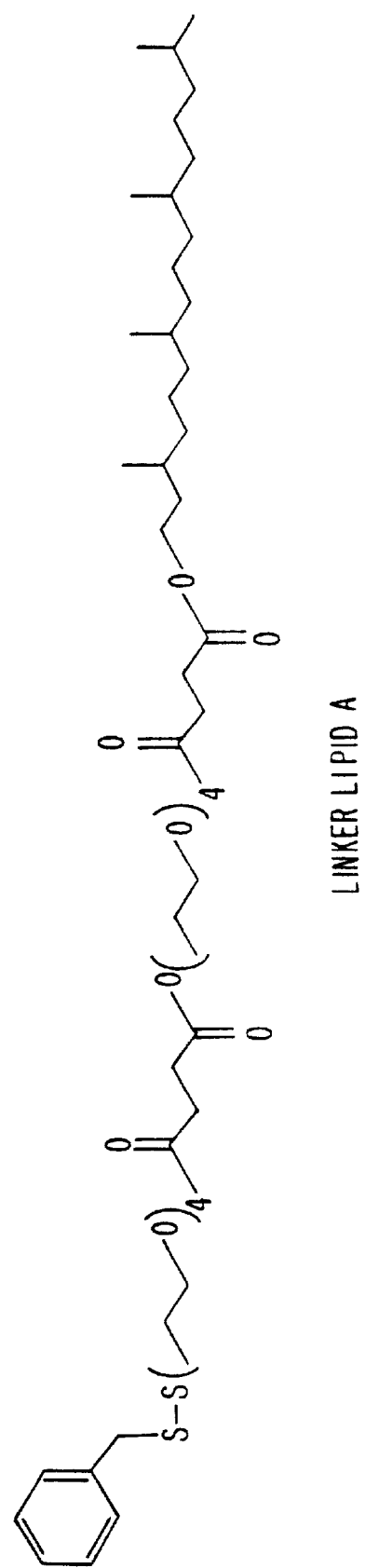
FIG. 1 shows Linker Lipid A which comprises a disulfide attachment region, a hydrophilic region composed (in sequence) of tetraethylene glycol, succinic acid, tetraethylene glycol, succinic acid subgroups and an aliphatic chain.
Figure 2:
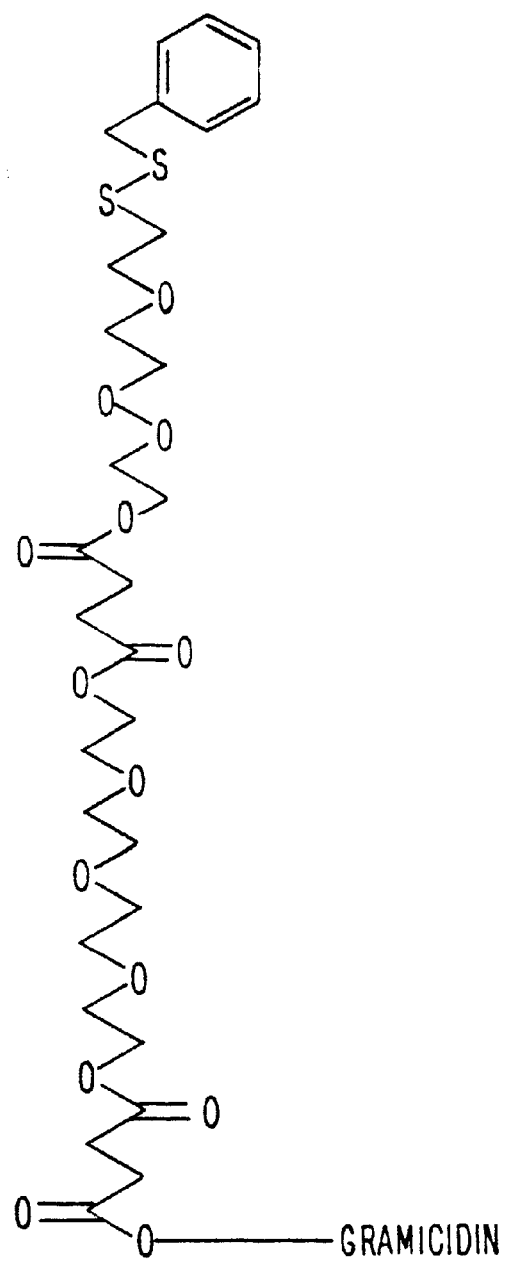
FIG. 2 shows a linker molecule which comprises a benzyl disulfide attachment region, a hydrophilic region composed (in sequence) of tetraethylene glycol, succinic acid, tetraethylene glycol, succinic acid, and a hydrophobic region of gramicidin.

EXAMPLE 1
Whole Blood K+ Detection in Monolayer Biosensor Membranes

Ion carriers other than gramicidin may be used in the membranes described in this invention. Simplified membranes formed mainly from membrane spanning lipid components can form extremely robust and biocompatible biosensors. Fewer membrane components also provides easier manufacturability.

Monolayer membrane:
  100 uM MSLPC (MSL-D)
  20 uM MAAD

Electrodes with freshly evaporated gold (1000 A) on chrome adhesion layer (200 A on glass microscope slides) were dipped into an ethanol solution of the above components, rinsed with ethanol, then stored at 4° C. under ethanol until used for impedance measurements (days-weeks). The slide was clamped into a blocked containing teflon coated wells which defined the area of the working electrode as approximately 16 mm$^2$. PBS buffer was added followed by 5 ul of 1 mM valinomycin in ethanol, an ionophore specific for K+ detection. Impedance measurements were carried out.

FIG. 7 shows that the impedance change showing the biosensor response to K+ in human whole blood (obtained from a healthy volunteer) was specific to the presence of valinomycin incorporated into the biosensor membrane. The volume of PBS buffer in the electrode well was completely exchanged for 100 ul whole blood which resulted in the decrease in impedance as K+ ions in blood were transported across the biosensor membrane by valinomycin. The addition of whole blood showed no detrimental effects to the lipid membrane.

Even more convenient assembly of the membrane would be with membrane components which are covalently linked together and synthesised as a single molecule. Thus a membrane spanning lipid can be linked to spacer molecules such as MAAD or its analogues (to provide correct packing of the first layer which enables essential ion channel or ionophore diffusion), and to extra hydrocarbon chains such as phytanyls to provide increased fluidizing properties to the membrane spanning lipid.

EXAMPLE 2
Repeated Whole Blood K+ Detection in Same Monolayer Biosensor Membrane The robust and biocompatible characteristics of the monolayer biosensor can be illustrated by its ability to sustain repeated exposure to whole blood and still function as a biosensor.

Monolayer membrane:
  100 uM MSL-succinic accid (MSL-D)
  20 uM MAAD

Electrodes were prepared and measured as described in Example 1. After addition of valinomycin, 80 ul PBS buffer was removed from the electrode well (160 ul initial volume) and replaced by 80 ul whole blood. After the change in impedance due to the K+ response was recorded, the well was washed 4 times with PBS buffer and valinomycin was again added to the well before the next exposure of whole blood. The cycle was repeated 4 times as shown in FIG. 8, showing the biosensor remaining intact and functioning even after repeated exposure to whole blood.

EXAMPLE 3
Whole Blood K+ Titration in Biosensor Membranes

This example shows that the detection ability of the biosensor is within the clinically-relevant range of 3–6 mM, and above, if required. The biosensor is also stable to whole blood addition even in the bilayer, rather than monolayer, configuration.

1st layer:
  100 uM MSL-PEG 400-COOH (MSL-D)
  0.8 mM MAAD
  1 mM DLP
2nd layer:
  14 mM (C18DPEPC:$C_{18}$GMPE=7:3): vahnomycin= 100:1
(Note: $C_{18}$DPEPC=DPEPC with 2 additional $CH_2$ groups: $C_{18}$GMPE=GDPE with a monophytanyl chain instead of diphytanyl chains and 2 additional $CH_2$ groups).

Electrodes were prepared as described in Example 1. The 2nd layer was added from an ethanolic solution then PBS buffer was added, and the electrode well was washed 4 times. Whole blood was added to different electrodes and the change of impedance with K+ concentration recorded. FIG. 9 shows that the biosensor response to K+ in human whole blood was a function of the concentration of K+ in the blood. The addition of whole blood showed no detrimental effects to the lipid membrane.

EXAMPLE 4
Detection of Endogenous Ferritin in Whole Blood and Serum

The bilayer biosensor is stable to whole blood addition and is fully functional for a single-step, endogenous ferritin detection in unprocessed blood. (Blood was obtained from a volunteer using CP2D as anticoagulant, which contains citric acid, sodium citrate, sodium acid phosphate, and dextrose).

1st layer:
  9.3 nM Gayy (Linker B)
  5.5 nM MSLXXB (MSL-C)
  1.1 uM MSLOH (MSL-D)
  37 uM MAAD
  75 uM DLP (Linker A)
2nd layer:
  14 mM (DPEPC:GDPE=7:3): Ga5XB (Linker E)=100,000:1

Figure 4:
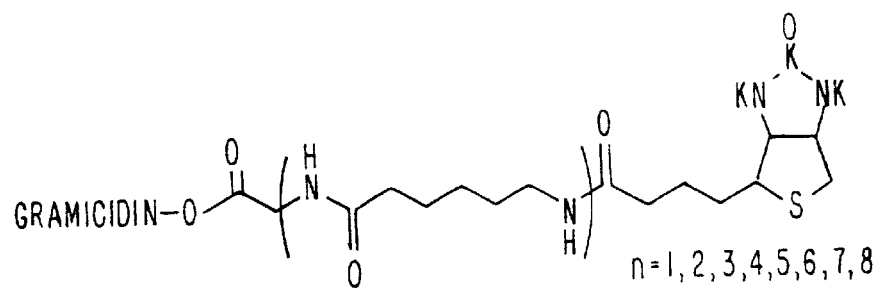
FIG. 4 shows biotinylated gramicidin E in which the biotin is attached to the gramicidin via the ethanolamine end using a linker arm that is made up of betveen 1 to 8 aminocaproyl groups.
Figure 5:
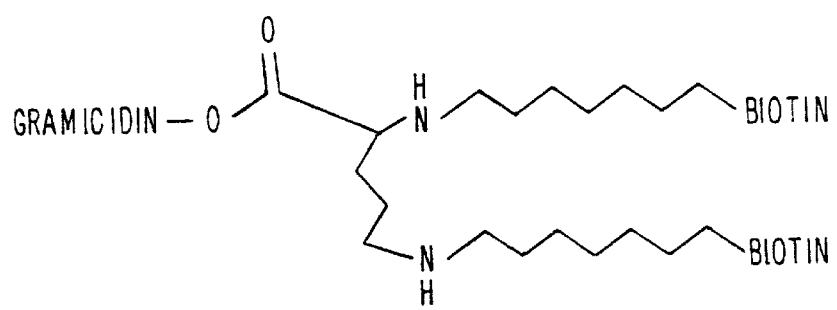
FIG. 5 shows two biotins attached to gramicidin via the ethanolamine end with each biotin attached to two to four linearly joined aminocaproyl groups that are attached to a lysine group.
Figure 6:
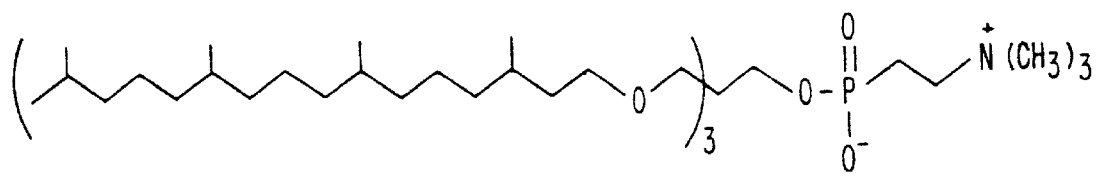
FIG. 6 shows a lipid consisting of a triphytanyl phosphoryl choline.
Figure 7A:
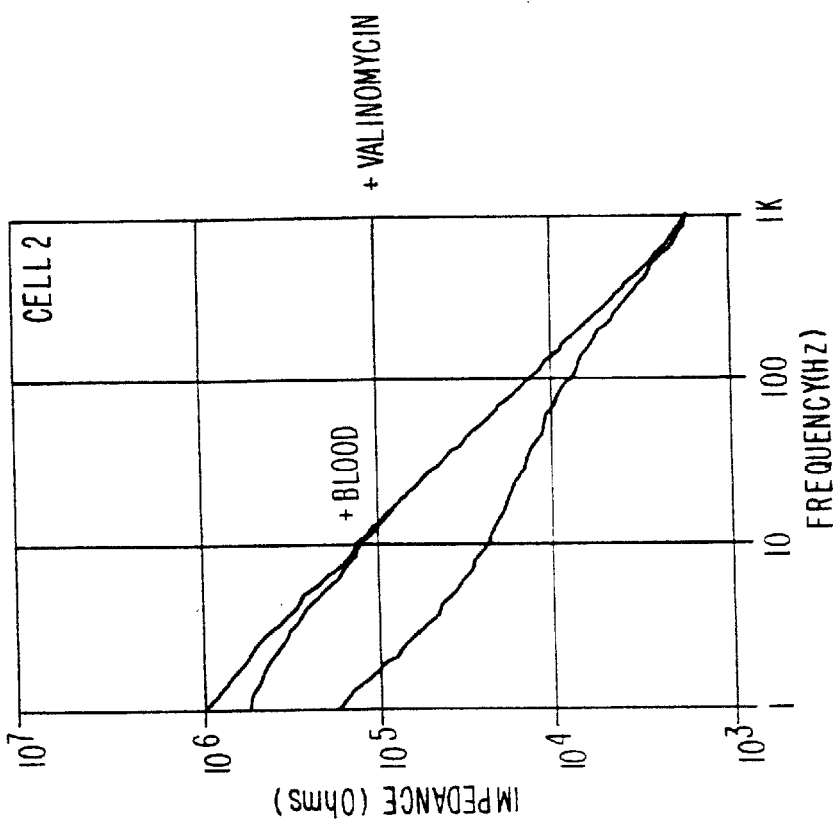
Figure 7B:
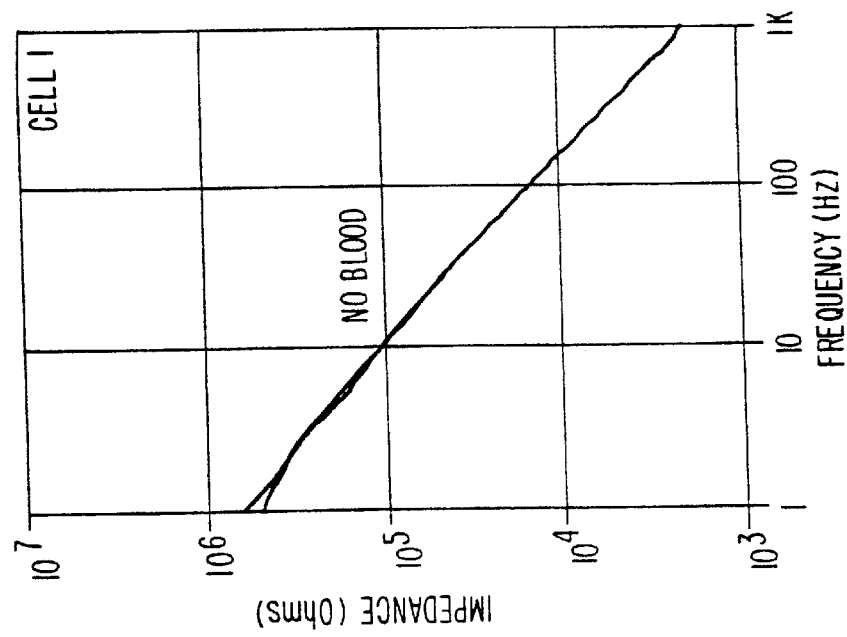
Figure 7D:
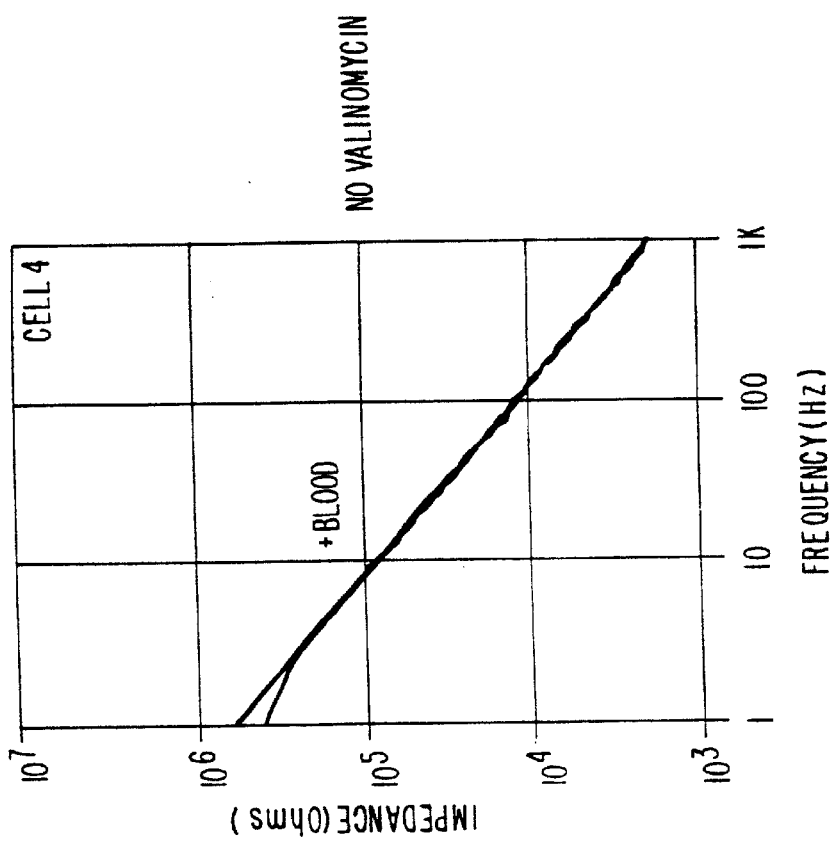
Figure 7C:
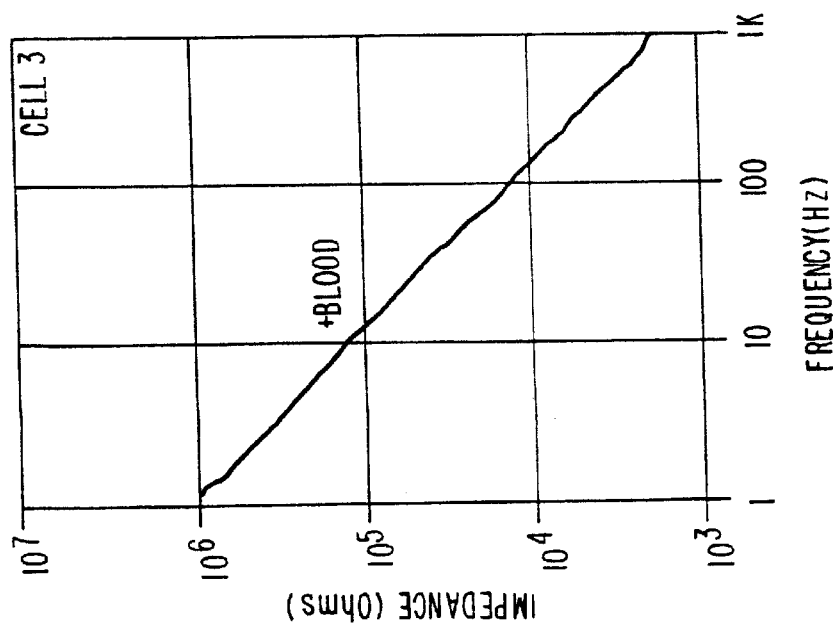
Figure 10A:
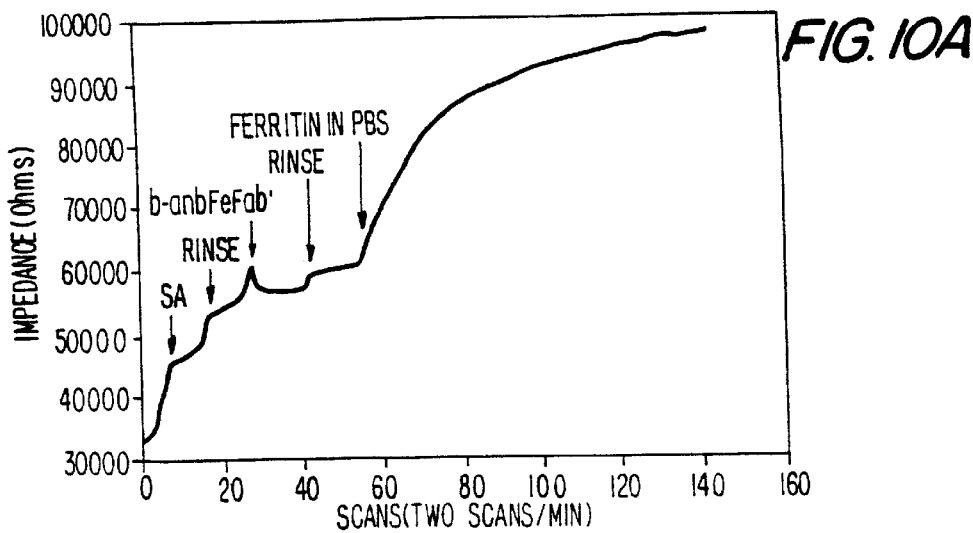
FIGS. 10A–10F shows the detection of ferritin in whole blood and serum.
Figure 10B:
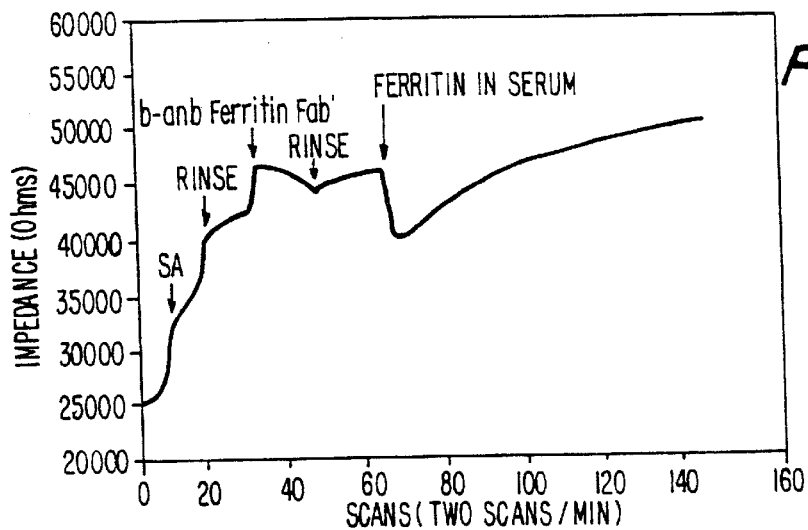
Figure 10C:
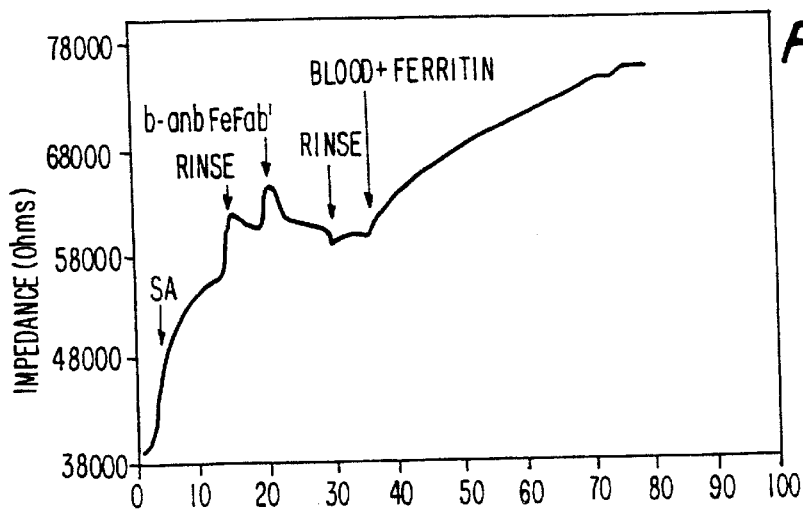

Electrodes were prepared and 2nd layer added as described in Example 3. Ferritin in either PBS, serum or whole blood was added to different electrodes [figures 10a), b), and c)], and the change of impedance with ferritin concentration was recorded. FIGS. 4 also shows the steps preceding the addition of analyte, i.e. when SA is added (5 ul 1 mg/ml in PBS), washing out excess SA, then in FIGS. 10a), b), and c) only, the addition of anti-ferritin Fab' biotinylated at the thiol group (5 ul 0.05 mg/ml in PBS) and the subsequent rinsing step. is also shown.

Figure 10D:
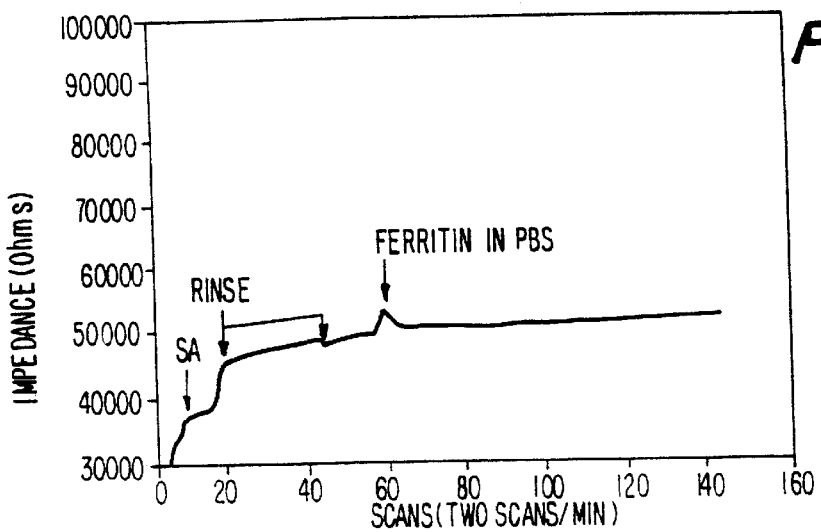
Figure 10E:
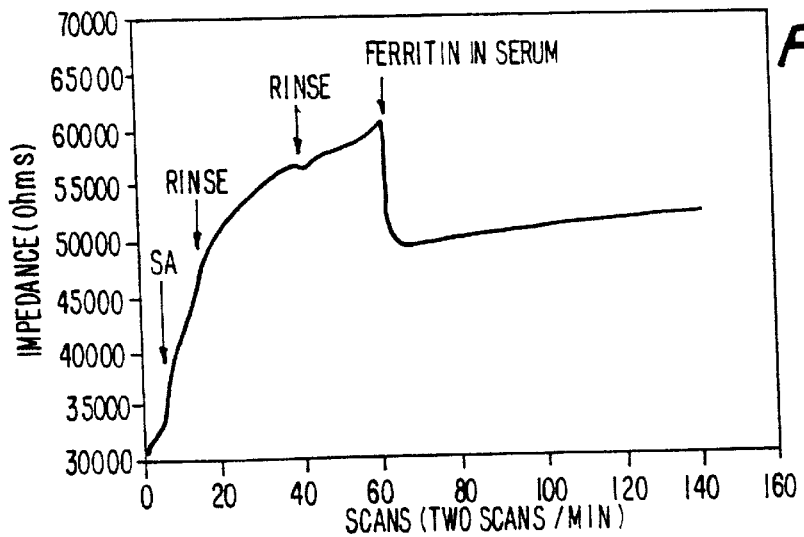
Figure 10F:
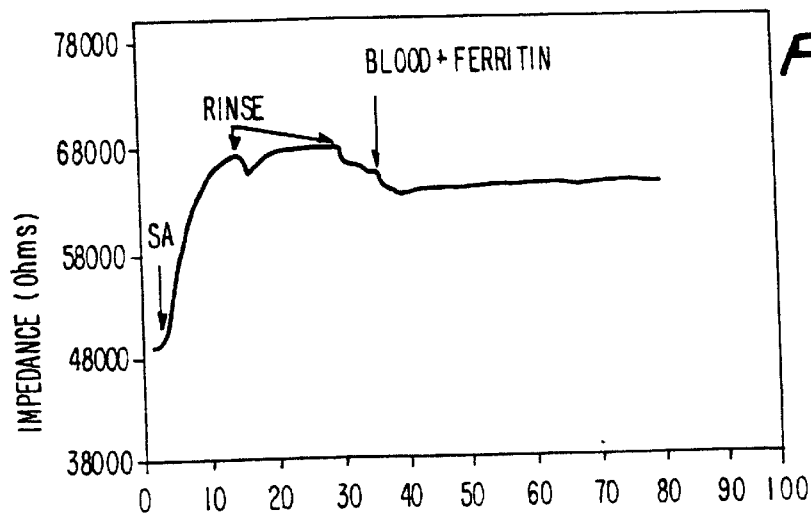

FIGS. 10d), e), and f) shows that in the absence of specific receptors for ferritin, there is no response, regardless of whether PBS, serum or whole blood was added. Note that no other reagents or washing steps are required after the sample containing the analyte has been added. The biosensor is manufactured up to the stage where specific receptors are added, then it is ready for the one-step addition of the sample.

EXAMPLE 5
Titration Curve from Endogenous Ferritin in Human Serum

After clotting, blood obtained from 4 different volunteers was centrifuged down and serum was separated and used for the present example.

1st layer:
- 9.3 nM Gayy (Linker B)
- 5.5 nM MSLXXXXB (MSL-C)
- 1.1 uM MSLOH (MSL-D)
- 37 uM MAAD
- 75 uM DLP (Linker A)

2nd layer:
- 14 mM (DPEPC:GDPE=7:3) Ga5XB (Linker E)=66,667:1

Figure 11:
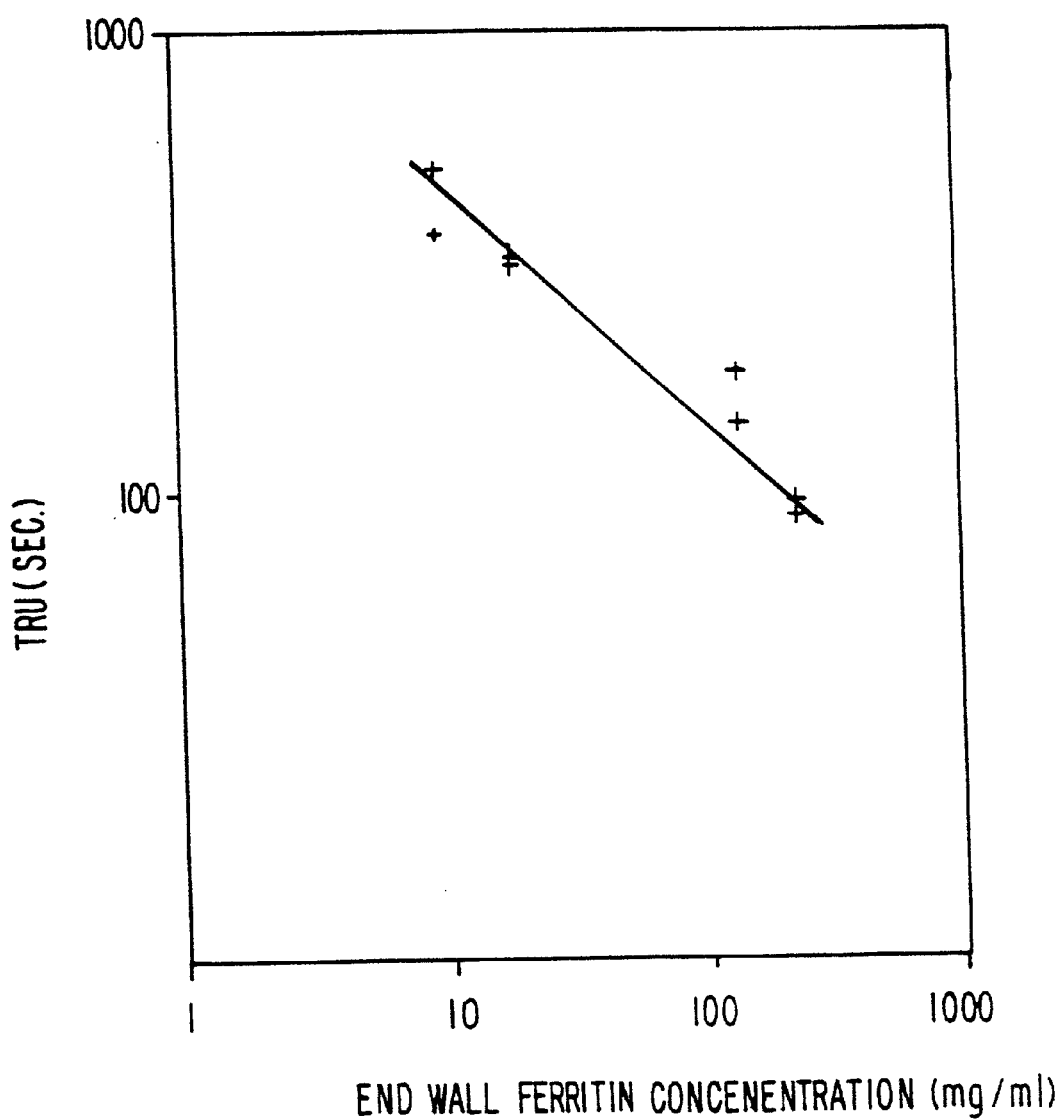
FIG. 11 shows the response of the biosensor to serum concentrations of ferritin.

Electrodes were prepared and 2nd layer added as described in Example 4. From the initial well volume of 150 ul, 100 ul buffer was removed and replaced with 150 ul serum. Different sera were added to different electrodes and the tau (s) of the ferritin response was calculated from the admittance at minimum phase. FIG. 11 shows the response of the biosensor to sera containing one of the following concentrations of ferritin (measured using the Immulite autoanalyser); 18.8, 38, 280, or 476 pM, in duplicate.

FIGS. 10d), e), and f) shows that in the absence of specific receptors for ferritin, there is no response, regardless of whether PBS, serum or whole blood was added. Note that no other reagents or washing steps are required after the sample containing the analyte has been added. The biosensor is manufactured up to the stage where specific receptors are added, then it is ready for the one-step addition of the sample.

EXAMPLE 6
Variation of Analyte Response with Gramicidin-biotin Linker Length and Type The linker length between gramicidin and biotin can be varied by adding varying numbers of caproyl groups, or by adding "multi-armed" linkers to gramicidin, each linker terminating with a biotin molecule, thus enabling a single gramicidin to capture either two biotin sites within the same SA molecule or two or more SA molecules, depending on the length of the linker and number of "arms" present.

1st layer:
- 0.1 uM Gayy (Linker B)
- 10 uM MSLXXB (MSL-C)
- 0.8 mM MAAD
- 1 mM DLP (Linker A)
- 10 mM GMPE 2nd layer:
- Ga . . . B=100,000:1, using either GaXB, GaXXB, GaXXXB, or Ga(XXX)$_2$ (Linkers E) 28 mM GMPE (Note: GMPE=GDPE with a monophytanyl chain instead of diphytanyl chains)

Figure 12:
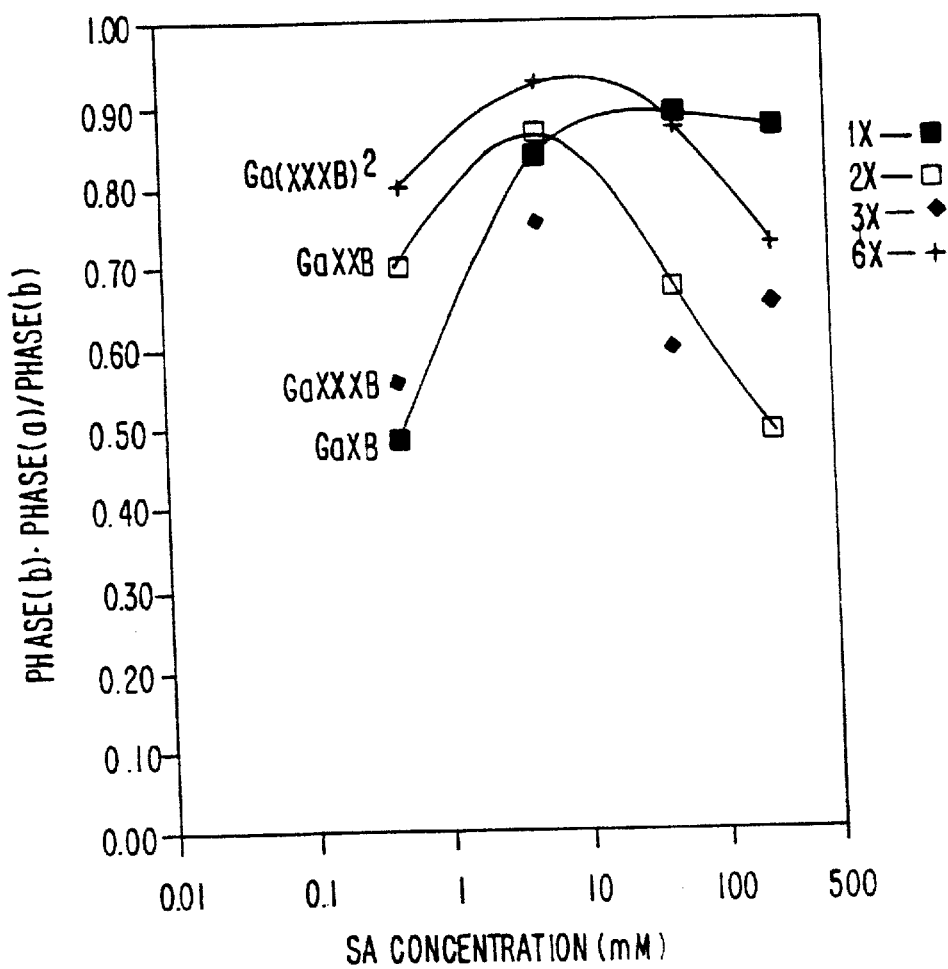
FIG. 12 shows the dependence of the streptavidin response on linker type and length.
Figure 13:
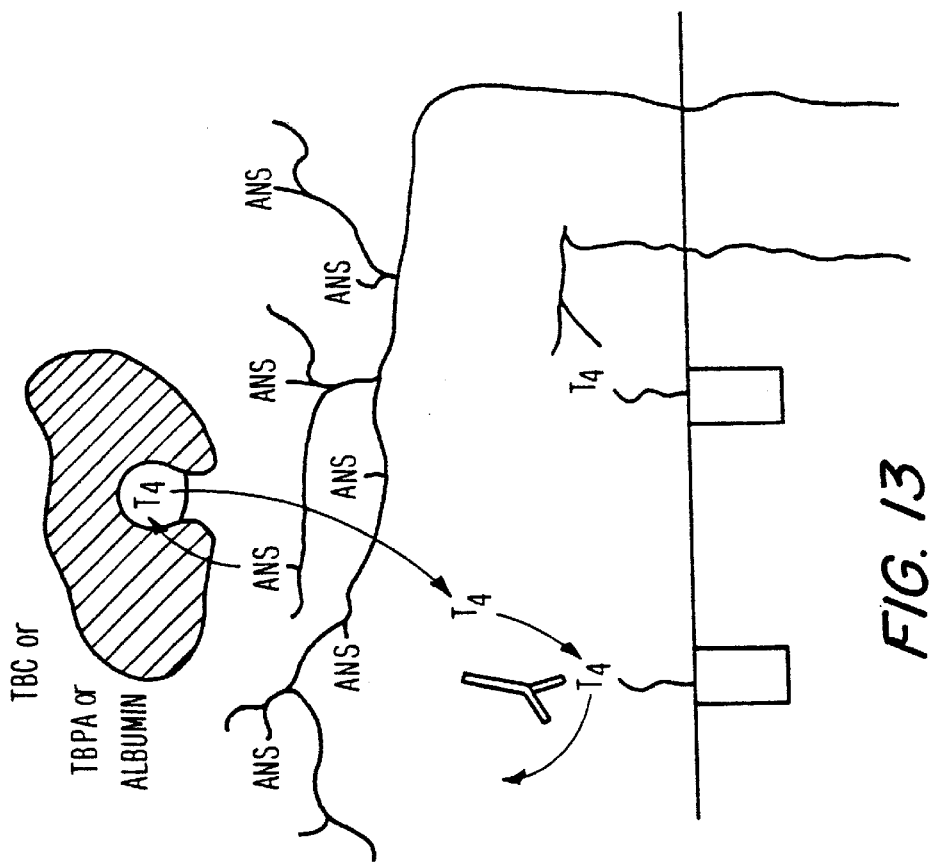
FIG. 13 shows a network of water-replacing agent (i.e. protectant substance) linked to the biosensor membrane, containing thyroxine displacement reagent such as ANS. As the ANS molecules compete for protein binding sites, thyroxine is released and diffuses to the membrane where it is detected by competitive assay (thyroxine-gramicidin bound to anti-thyroxine Ab/Fab which is bound to membrane spanning lipids, is competed off with the released thyroxine, leading to the release of gramicidin channels and return of ionic conduction in the biosensor).

Electrodes were prepared and 2nd layer added as described in Example 4. SA was titrated into membranes containing the different types of gramicidin. FIG. 12 shows the dependence of the SA response on linker type and length. The response was measured by normalising the frequency at the phase minima, i.e. calculating $$(\text{phase}_{final} - \text{phase}_{initial}) / \text{phase}_{final}.$$

EXAMPLE 7
Preparation of Bilayer Membrane

The structure of "linker lipid A" is shown in FIG. (1); the structure of "linker gramicidin B" is shown in FIG. (2); the structure of "membrane spanning lipid D" is shown in figure (3); the structure of "membrane spanning lipid C" where n=2 is shown in FIG. (3), the structure of "biotinylated gramicidin F" used is shown in FIG. (5), the structure of "biotinylated gramicidin E" used, where n=5, is shown in FIG. (4).

A glass slide or plastic support is evaporatively coated with a 50 angstrom chromium adhesion layer. followed by a 2000 angstrom layer of gold. The gold coated substrate is placed in an ethanolic solution containing "linker lipid A" (300 ul of 10 mM solution in ethanol), the disulfide of mercaptoacetic acid (150 ul of a 10 mM solution in ethanol), "linker gramicidin B" (100 ul of a 0.01 mg/ml solution in ethanol), "membrane spanning lipid D" (225 ul of a 1 mM solution in ethanol), "membrane spanning lipid C" (22.3 ul of a 0.01 mM solution in ethanol) and ethanol (50 ml). The gold coated substrate should preferably be placed into this solution within five minutes of preparation. The gold coated substrate is left in this solution for 60 minutes and then rinsed with ethanol. The slide may then be stored in ethanol, water+sodium azide (0.01% w/v), ethylene glycol, glycerol, decane, decanol or hexadecane until required. When needed, the gold coated slide is rinsed with ethanol and is then assembled in an electrode holder such that an electrode is defined, that for the current examples has an area of approximately 16 mm$^2$. Then 5 ul of a solution of 1,2-di(3RS,7R,11R-phytanyl)-glycero-3-phosphocholine and 1,2-di(3RS,7R,11R-phytanyl)glycerol in a 7:3 ratio, 14 mM total lipid concentration in ethanol is added to the surface of the gold electrode and then rinsed with two washes of 500 ul of phosphate buffered saline (PBS), leaving 100 ul PBS above the electrode surface. A counter electrode, typically silver, is immersed in the PBS solution; and the counter electrode and the sensing electrode are connected to an impedance bridge. A DC offset of −300 mV is applied to the sensing electrode during the AC measurement.

EXAMPLE (8)
Preparation of Solubilised Gramicidin

Example (8A)

A solution of "linker gramicidin E" (1 uM) and sodium dodecylsulfate (10 uM) in PBS is sonicated in a bath sonicator for 20 minutes. This solution may be stored for at least 12 months at 4° C. Although the gramicidin with sodium dodecylsulfate is stable in aqueous solution, the gramicidin incorporates readily into sensing membranes and produces conducting ion channels. This change in conduction can be monitored using impedance spectroscopy.

Example (8B)

Alternatively, a solution of "linker gramicidin F" (20 ul of 10 uM in ethanol) was added to a solution of streptavidin (200 ul of 1 mg/ml in PBS+700 ul of PBS, total volume 1 ml) and mixed by vortexing for 1 minute. This solution is stable for several months at 4° C.

In the absence of either SDS or streptavidin, the ability for the gramicidin to insert into the bilayer membrane is deteriorates rapidly over one to two days. Not wishing to be bound by scientific theory, it is assumed that the gramicidin precipitates out of the aqueous solution.

EXAMPLE (9)
Preparation of a Biosensor Membrane Using Solubilised Gamicidin

Example (9A)

Figure 14:
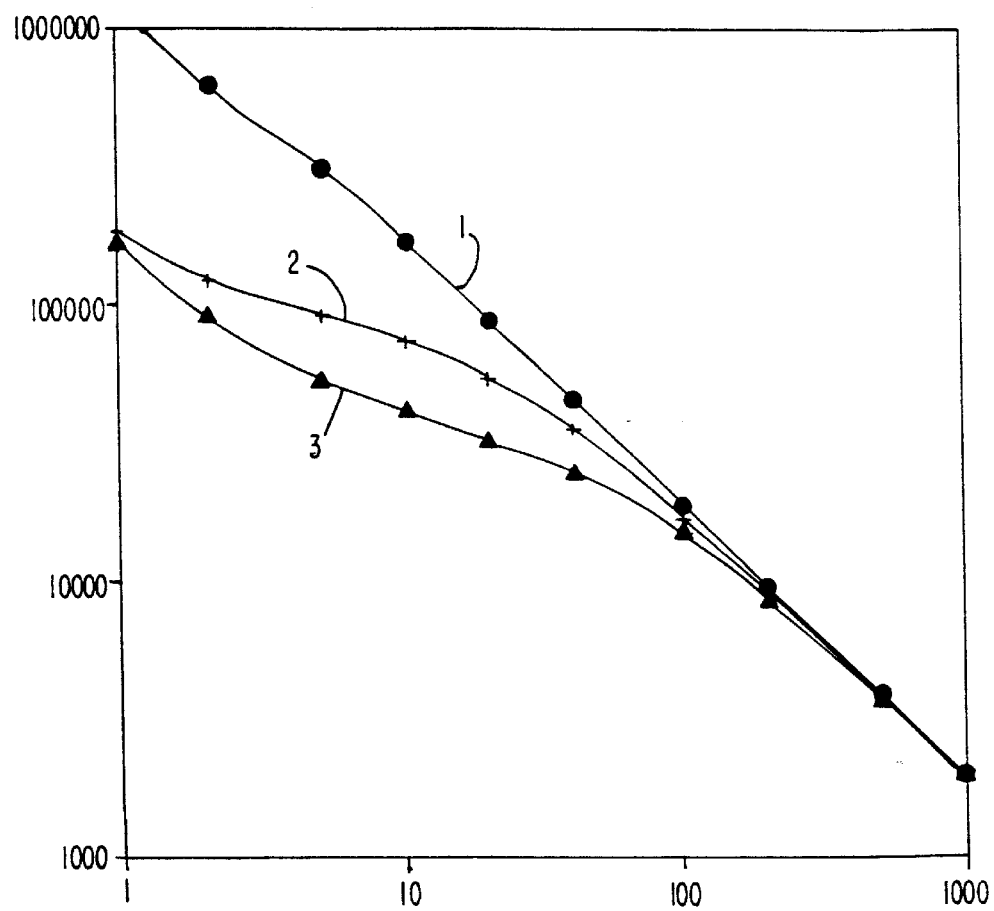
FIG. 14 shows the impedance spectra of a membrane prior to addition of "linker gramicidin E"/SDS (1); after the addition of "linker gramicidin E"/SDS and after addition of streptavidin and biotinylated anti-ferritin Fab' (2); and the spectrum after the addition of ferritin (3).

To the bilayer membrane prepared in example (7) is added a solution (10 ul)of solubilised gramicidin prepared in example 8A. The conductance of the membrane is monitored by impedance spectroscopy. This conductance increases as gramicidin molecules insert into the bilayer membrane. Addition of equivalent amounts of SDS or streptavidin without any gramicidin do not cause significant increases in conduction of the membrane. Prior to addition of the solubilised gramicidin the impedance at 10 Hz was 170 kohm/16 mm$^2$. After addition of the solubilised gramicidin the impedance was monitored until the desired level of conductance had been achieved, (in this case an impedance of 41 kohms/16 mm$^2$ at 10 Hz) the electrode well was rinsed with PBS (3×500 ul). Streptavidin (5 ul of 0.1 mg/ml in PBS) is added to the electrode well, left for three to five minutes and rinsed with PBS (3×500 ul). In the case of a ferritin responsive sensor, biotinylated anti-ferritin Fab' (5 ul of 0.06 mg/ml in PBS) was added and after three to five minutes the electrode well was rinsed with PBS. In the case of a thyroid stimulating hormone (TSH) sensor a 1:1 mixture of two complementary biotinylated anti-TSH Fab's (10 ul of 0.01 mg/ml) was added. The biotinylated Fab's were biotinylated via the free thiol group of freshly cleaved (Fab)$_2$ dimers. The sensor is now ready for addition of the analyte solution. Addition of a test solution of ferritin in PBS such that the final well concentration was 200 pM of ferritin gave an increase in impedance from 41 kohms/16 mm$^2$ to 74 kohms/16 mm$^2$. The impedance spectra are shown in FIG. 14.

Example (9B)

Figure 15:
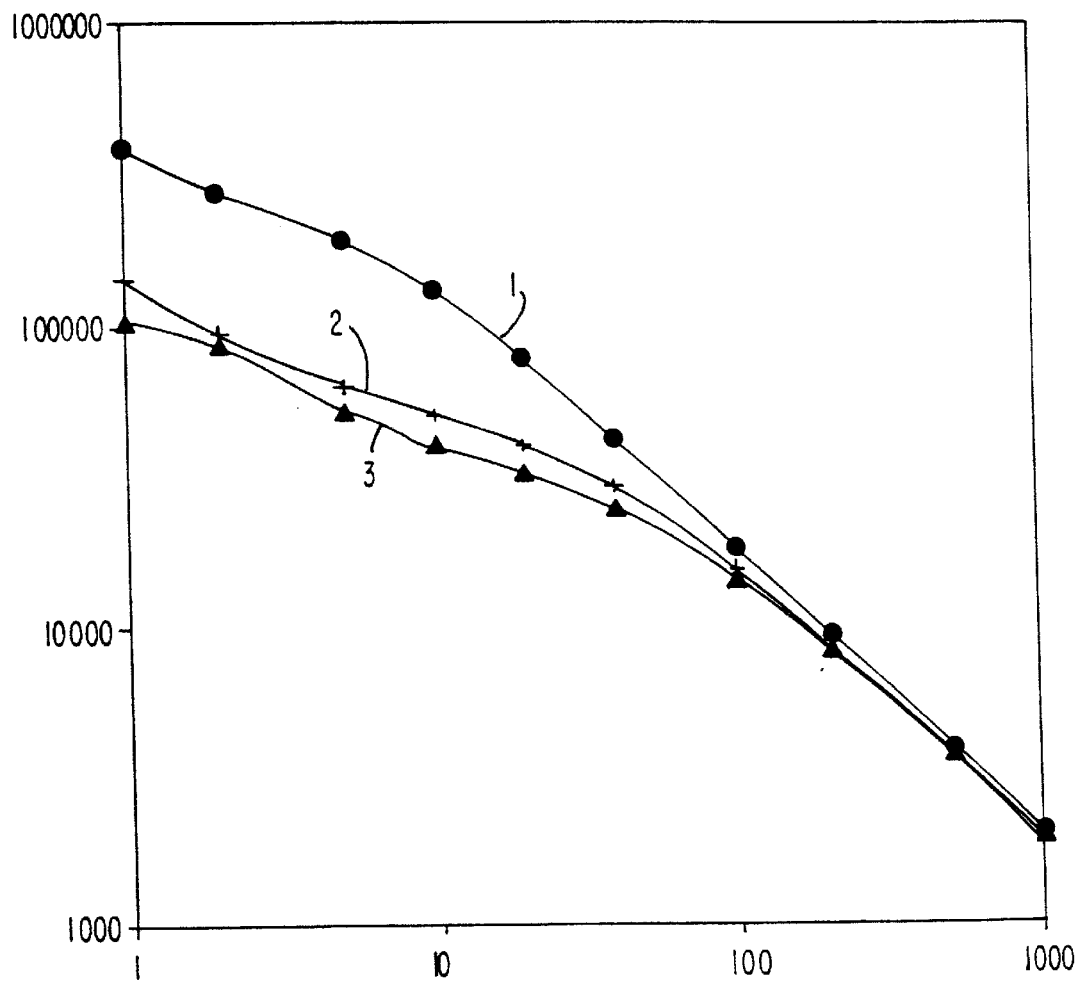
FIG. 15 shows the impedance spectra of a membrane prior to addition of "linker gramicidin F"/streptavidin (1); after the addition of "linker gramicidin F"/streptavidin and after the addition of biotinylated anti-TSH Fab's (2); and the spectrum after the addition of TSH (3).

To the bilayer membrane prepared in example (7) is added a solution of streptavidin (5 ul of 0.1 mg/ml in PBS). After three to five minutes the electrode well is rinsed with PBS and one of a complementary pair of biotinylated anti-TSH Fab' (10 ul of 0.01 mg/ml in PBS) is added. After 3 to 5 minutes the electrode is rinsed with PBS and a solution of solubilised gramicidin as prepared in example (8B) (10 ul) is added. The impedance of the membrane is monitored until the desired conduction is achieved ( in this case an impedance of 49 kohm/16 mm$^2$ at 10 Hz) and the electrode is then rinsed with PBS. The other of the complementary pair of biotinylated anti-TSH Fab' (10 ul of 0.01 mg/ml in PBS) is then added and after three to five minutes the electrode is rinsed. The sensor now has the first of the complementary anti-TSH Fab' attached to the "membrane spanning lipid C" and the second of the complementary anti-TSH Fab' attached to "linker gramicidin F". Addition of a test solution of TSH in PBS such that the final analnicyte concentration in the well was 500 pM gave an increase of impedance from 49 kohm/16 mm$^2$ to 60 kohm/16 mm$^2$. The impedance spectra are shown in FIG. 15.

EXAMPLE (10)
Dry Storage of Sensor Membrane

Example (10A)

Sensor membranes were prepared as in example (7). The sensor membranes were then rinsed with a 0.5% (w/v) glycerol in water solution (+0.1% sodium azide). Excess glycerol solution was removed such that 20 ul of the glycerol solution was left in the electrode well assembly. The sensor membrane was then placed in a chamber containing dessicant (RH in chamber was approximately 15%) and allowed to dry. The dry sensor membrane could then be stored at 15%–70% RH at room temperature for up to 1 week. It was found that when the membranes were dried from solutions with glycerol concentrations of less than 0.1% w/v the membranes became excessively leaky on rehydration with PBS. Thus, the impedance at 10 Hz for a freshly prepared, sealed membrane that has not been dried was between 129–149 kohm/16 mm$^2$, while the impedance at 10 Hz for membranes that had been dried from 5–0.1% w/v glycerol solution was between 100–110 kohm/16 mm$^2$. Membranes that had been dried from less than 0.1% w/v glycerol solution became very leaky with 10 Hz impedances of less than 45 kohm.

| Impedance at 10 Hz (average of 16 electrodes): | | |
|---|---|---|
| | Freshly prepared | 5 days at 15% RH |
| 5% glycerol w/v | 148 kohm | 118 kohm |
| 0.5% glycerol w/v | 139 kohm | 98 kohm |
| 0.1% glycerol w/v | 148 kohm | 103 kohm |
| 0.05% glycerol w/v | 136 kohm | 35 kohm |

One of the advantanicgeous properties of excess drying agent is that it protects the bilayer lipid membrane from passing through an air/water interface. The air/water interface may destabilise and disrupt certain lipid bilayer structures. The glycerol coating allows for controlled rehydration of the lipid membrane without the lipid bilayer immediately contacting the air/water interface as the analyte solution is added, as the rate of dissolution of the glycerol is slower than the rate of addition of the analyte solution.

It was found that if the sensor membrane was stored at <50% RH then on addition of analyte solution an equilibration/rehydration period occurred that lasted 30–90 seconds. This equilibration is not necessarily a problem when determining analyte concentration as it may be subtracted using a second non-sensing differential electrode. However, it is also possible to remove this equilibration/rehydration effect by pre-equilibrating the dry sensor membranes for a period of time in an atmosphere of RH of approximately 70%. Typically this pre-equilibration may be for 5–90 minutes prior to addition of analyte solution.

Example (10B)

Sensor membranes were prepared as in example (7) except that "linker gramicidin E" was incorporated into the bilaver at lipid:gramicidin ratio of 4,0000:1. The membranes were dried from 0.5% w/v glycerol solution as described in example (10A) and were subsequently stored for 5 days at room temperature at approximately 15% RH. The sensor membranes were then rehydrated with PBS solution and streptavidin was added (5 ul of 0.1 mg/ml). The rate of increase in the impedance was measured. A convenient measure was the frequency at the minimum phase taken from a standard Bode plot of the phase versus time. An exponential curve ($y=-ke^{t/tau}$) was fitted to the response rate curve and as a measure of the rate of gating towards the streptavidin the tau value was used. The tau value is related to the analyte concentration. It was found that over a period of five days the tau value in response to streptavidin gating did not vary within experimental error. Thus:

| Days of Storage | Tau (s), (std. deviation) |
| --- | --- |
| 0 | 71 (26) |
| 1 | 79 (14) |
| 2 | 56 (12) |
| 3 | 80 (27) |
| 5 | 77 (16) |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of producing an electrode membrane combination comprising:
   (1) Forming a first solution containing Linker Lipid A, disulfide of mercaptoacetic acid (MAAD)or similar molecule, linker Gramicidin B, membrane spanning lipid C (MSL-C) and membrane spanning lipid D (MSL-D) or other suitable linker molecules and other ion channel or ionophore combinations;
   (2) Contacting an electrode containing a clean gold surface with the solution to allow the disulfide containing components of said solution being adsorbed onto the gold surface of the electrode;
   (3) Rinsing the electrode with a suitable organic solvent; and
   (4) Removing the excess organic solvent used for rinsing;
   (5) Adding a solution of lipid and biotinylated gramiciden E dispersed in a suitable solvent onto the electrode surface containing the first solution;
   (6) Rinsing the electrode surface with an aqueous solution;
   (7) Adding a solution of streptavidin, avidin, neutavidin, avidin or streptovidin derivative;
   (8) Rinsing the electrode with an aqueous solution to remove excess streptavidin avidin, neutavidin, avidin or streptovidin derivative;
   (9) Adding a solution of a biotinylated binding partner molecule; and
   (10) Rinsing the coated electrode with an aqueous solution.

2. A method according to claim 1, wherein the lipid used in step (1) is a mixture of diphytanyl phospatidyl choline (DPEPC) and glyceryl diphytanyl ether (GDPE).

3. A method according to claim 1, wherein the DPEPC and GDPE is in a 7:3 ratio.

4. A method according to claim 1, wherein the lipid used in step (1) is a triphytanyl phosphoryl choline as shown in FIG. (6).

5. A method according to claim 1, wherein 0–50% cholesterol is incorporated into the lipids used in step (1).

6. A method according to claim 1, wherein 0–20% cholesterol is incorporated into the lipids used in step (1).

7. A method according to claim 1, wherein the ratio of lipid to biotinylated gramicidin E is between 10,000:1 and 1,000,000:1.

8. A method according to claim 7, wherein the ratio of lipid to biotinylated nicgramicidin E is 100,000:1.

9. A method according to claim 1, wherein the boitin is attached to the gramicidin via the ethanolamine end using a linker arm that is made up of between 1–8 aminocaproyl groups.

10. A method according to claim 9, wherein the biotins are attached to the gramicidin via the ethanolamine end such that each biotin is attached to 2 to 20 aminocaproyl groups arranged as a branched structure.

11. A method according to claim 1, wherein two boitins are attached to the gramicidin at the ethanolamine end such that the biotins are able to bind simultaneously into the adjacent binding sites of a streptavidin, avidin or a similar biotin-binding protein.

12. A method according to claim 11, wherein the two biotins are attached to the gramicidin via the ethanolamine end such that each biotin is attached to 2 to 4 linearly joined animocaproyl groups that are attached to a lysine groups as shown in FIG. (5).

13. A method according to claim 11, wherein the biotins are attached to the gramicidin via the ethanolamine end such that each biotin is attached to 2 to 20 linearly joined aminocaproyl groups that are attached to a lysine groups.

14. A method according to claim 1, wherein two biotins are attached to the gramicidin at the ethanolamine end such that the biotins are able to bind simultaneously into two separate streptavidin, avidin or a similar biotin-binding protein molecules.

15. A method according to claim 1, wherein the amount of streptavidin, avidin or other similar biotin-binding protein that is added in step (3) is sufficient to cause a prozone effect, allowing most of the available biotinylated species in the membrane to have one streptavidin or related molecule bound to prevent cross-linking between gramicidin channels and MSL until a sample containing analyte is added to the sensor.

16. A method according to claim 1, wherein prior to the addition of streptavidin, avidin or similar biotin-binding protein, the lipid membrane electrode assembly is cooled.

17. A method according to claim 16, wherein the lipid membrane electrode assembly is cooled to betveen 0° and 50° C.

18. A method according to claim 17, wherein the lipid membrane electrode assembly is cooled to between 0° and 5° C.

19. A method according to claim 16, wherein the subsequent rinsing and addition of the biotinylated binding partner molecule is carried out at 0° to 50° C.

20. A method according to claim 19, wherein the subsequent rinsing and addition of the biotinylated binding partner molecule is carried out at 0° to 5° C.

21. A method according to claim 19, wherein the linker between the Fab' and biotins is between 10–80 angstroms in length.

22. A method according to claim 19, wherein the binding partner colecule is a biotinylated antibody or biotinylated antibody fragment.

23. A method according to claim 22, wherein the linker between the Fab' and biotins consists in 1–8 aminocaproyl groups.

24. A method according to claim 22, wherein the group containing two biotins is attached to the antibody or antibody fragment such that the two biotins are able to simultaneously complex one streptavidin, avidin or other similar biotin-binding proteins.

25. A method according to claim 22, wherein the group containing two biotins is attached to the antibody or antibody fragment such that the two biotins are able to complex simultaneously two streptavidin, avidin or other similar biotin-binding proteins.

26. A method according to claim 16, wherein the binding partner molecule is a Fab' fragment that is biotinylated via the free Fab' thiol group.

27. A method according to claim 1, wherein the steps (3) to (5) are substituted with:
   (3) Adding a solution containing a conjugate between streptavidin, avidin, neutravidin or other avidin or streptavidin derivative and a molecule which is a member of a binding pair.

28. A method according to claim 27 wherein the binding partner molecule is an antibody fragment such as a Fab, Fab' or Fabv fragment.

29. A method according to claim 27, wherein the binding pairs selected from: naturally occurring binding proteins and cellular receptors/analytes, enzymes or enzyme analogues/substrates, lectins/carbohydrates, complementary nucleic acid sequences, and FC, Protein A or Protein G/antibody.

30. A method according to claim 1, wherein the first solution contains the disulfide of mercaptoacetic acid (MAAD) or 2-mercaptoethanol (EDS).

31. A method according to claim 30, wherein the ratio of Linker Lipid A to the disulfide of mercaptoacetic acid (MAAD) or 2-mercaptoethanol (EDS) is 2:1.

32. A method according to claim 30, wherein the ratio of (Linker Lipid A+MAAD or EDS) to MSL-D is in the range of 10:1 to 100:1.

33. A method according to claim 30, wherein the ratio of (Linker Lipid A+MAAD or EDS) to MSL-C is between 20,000:1 to 100:1.

34. A method according to claim 30, wherein the ratio of (Linker Lipid A+MAAD or EDS) to MSL-C is 20,000:1.

35. A method according to claim 1, wherein the solution contains linker Gramicidin B rather than another suitable linker molecule/ion channel or other combination.

36. A method according to claim 35, wherein the ratio of (Linker Lipid A+MAAD or EDS) to linker Gramicidin B is 10,000:1.

37. A method according to claim 35, wherein the ratio of (Linker Lipid A+MAAD or EDS) to linker Gramicidin B is between 20,000:1 and 100,000:1.

38. A method according to claim 1, wherein the gold electrode surface consists of a freshly evaporated or sputtered gold electrode.

39. A method according to claim 38, wherein the gold electrode surface is freshly clean using a plasma etching process or an ion beam milling process.

40. A method according to claim 1, wherein the solvent component in the first solution and the organic solvent used for rinsing said first solution is ethanol.

* * * * *